(12) United States Patent
Carlessi et al.

(10) Patent No.: US 10,434,468 B2
(45) Date of Patent: Oct. 8, 2019

(54) METHOD AND SYSTEM FOR REMOVING AMMONIA FROM A VENT GAS STREAM OF A UREA PLANT

(71) Applicant: SAIPEM S.p.A., San Donato Milanese (IT)

(72) Inventors: Lino Carlessi, Dalmine (IT); Lorenzo Bruno, San Donato Milanese (IT); Rosario Galati, Pogliano Milanese (IT)

(73) Assignee: Saipem S.p.A., San Donato Milanese (IT)

( * ) Notice: Subject to any disclaimer, the term of this patent is extended or adjusted under 35 U.S.C. 154(b) by 123 days.

(21) Appl. No.: 14/768,404

(22) PCT Filed: Feb. 25, 2014

(86) PCT No.: PCT/IB2014/059242
§ 371 (c)(1),
(2) Date: Aug. 17, 2015

(87) PCT Pub. No.: WO2014/128682
PCT Pub. Date: Aug. 28, 2014

(65) Prior Publication Data
US 2016/0001224 A1   Jan. 7, 2016

(30) Foreign Application Priority Data

Feb. 25, 2013   (IT) .............................. MI2013A0268

(51) Int. Cl.
*B01D 53/58*   (2006.01)
*B01D 53/86*   (2006.01)
(Continued)

(52) U.S. Cl.
CPC ......... *B01D 53/58* (2013.01); *B01D 53/8634* (2013.01); *B01D 53/90* (2013.01);
(Continued)

(58) Field of Classification Search
None
See application file for complete search history.

(56) References Cited

U.S. PATENT DOCUMENTS

| | | | |
|---|---|---|---|
| 2,046,827 A | 7/1936 | Lawrence et al. | |
| 3,522,305 A | 7/1970 | Olson | |
| 4,330,513 A * | 5/1982 | Hunter | B01D 53/72 422/139 |

(Continued)

FOREIGN PATENT DOCUMENTS

| | | |
|---|---|---|
| DE | 33 08 406 A1 | 9/1983 |
| DE | 41 16 362 A1 | 11/1992 |

(Continued)

OTHER PUBLICATIONS

Notification Concerning Submission, Obtention or Transmittal of Priority Document (Form PCT/IB/304) for International Application No. PCT/IB2014/059242 dated May 19, 2014.

(Continued)

*Primary Examiner* — Anita Nassiri-Motlagh
(74) *Attorney, Agent, or Firm* — Neal, Gerber & Eisenberg LLP (57) ABSTRACT

A method of removing ammonia from a continuous vent gas stream of a urea plant, in particular of a medium-pressure section of a urea plant, includes a step of removing ammonia from the continuous vent gas stream of the urea plant using a controlled-combustion process including at least a first lean, oxygen-poor combustion step performed in the presence of an understoichiometric amount of oxygen acting as the sole comburent, and in a reducing atmosphere of hydrogen.

20 Claims, 5 Drawing Sheets

(51) Int. Cl.
*C07C 273/04* (2006.01)
*B01D 53/90* (2006.01)

(52) U.S. Cl.
CPC ...... *C07C 273/04* (2013.01); *B01D 2251/102* (2013.01); *B01D 2251/11* (2013.01); *B01D 2251/20* (2013.01); *B01D 2257/406* (2013.01); *Y02A 50/2346* (2018.01)

(56) References Cited

U.S. PATENT DOCUMENTS

| 5,934,892 | A | * | 8/1999 | Rabovitser | ............... | F23B 5/00 |
| | | | | | | 431/10 |
| 2007/0059228 | A1 | | 3/2007 | Nalette et al. | | |
| 2009/0226353 | A1 | | 9/2009 | Tekie et al. | | |

FOREIGN PATENT DOCUMENTS

| EP | 2 505 581 | | 10/2012 | | |
| GB | 2116531 | | 9/1983 | | |
| GB | 2116531 | B * | 11/1985 | ............. | B01D 53/58 |
| WO | WO 2008/141832 | | 11/2008 | | |
| WO | WO 2010/006757 | | 1/2010 | | |
| WO | WO 2011/048461 | | 4/2011 | | |
| WO | WO 2011/089635 | | 7/2011 | | |
| WO | WO 2012/134288 | | 10/2012 | | |

OTHER PUBLICATIONS

International Search Report and Written Opinion for International Application No. PCT/IB2014/059242 dated Jun. 23, 2014.
PCT Demand (Form PCT/IPEA/401) for International Application No. PCT/IB2014/059242 and Reply dated Dec. 23, 2014.
Notification of Receipt of Demand by Competent International Preliminary Examining Authority (Form PCT/IPEA/402) for International Application No. PCT/IB2014/059242 dated Mar. 6, 2015.
Second Written Opinion of the International Preliminary Examining Authority for International Application No. PCT/IB2014/059242 dated Feb. 4, 2015.
Second Reply to the Written Opinion for International Application No. PCT/IB2014/059242 dated Apr. 1, 2015.
Notification of Transmittal of the International Preliminary Report on Patentability for International Application No. PCT/IB2014/059242 dated Jun. 10, 2015.
Notice of Opposition to European Patent No. EP2958659 dated Dec. 20, 2017.
Notice of Opposition to European Patent No. EP2958659 dated Jan. 4, 2018.
"Paper 10 From Flaring to Environmental Friendly Ammonia Firing and that Even done in an Economical Way," $12^{th}$ Stamicarbon Urea Symposium, May 2012.
Muir, John, "Nitrogen Oxides (NOx), Why and How They are Controlled," Environmental Protection Agency Technical Bulletin, Nov. 1999.
"Sustainability Driving the Future," $25^{th}$ AFA International Fertilizer Technology Conference Program, Jul. 9-11, 2012.
Steinebrunner, Klaus, "Verbrennung NH3-haltiger Prozessgase" Chem.-Ing.Tech. 67, pp. 199-202, Nov. 1995.
Submission in opposition proceedings made following summons to attend oral proceedings to European Patent No. EP2958659 dated Dec. 6, 2018.

* cited by examiner

METHOD AND SYSTEM FOR REMOVING AMMONIA FROM A VENT GAS STREAM OF A UREA PLANT

PRIORITY CLAIM

This application is a national stage application of PCT/IB2014/059242, filed on Feb. 25, 2014, which claims the benefit of and priority to Italian Patent Application No. MI2013A000268, filed on Feb. 25, 2013, the entire contents of which are each incorporated by reference herein.

BACKGROUND

As is known, urea is produced industrially using processes based on the high-temperature, high-pressure reaction of carbon dioxide and ammonia to form ammonium carbamate, and on the subsequent decomposition reaction of the ammonium carbamate to form urea and water.

In a typical urea plant (i.e., urea production plant), these processes are normally conducted in a synthesis section comprising a urea synthesis reactor; and the urea and water solution produced in the synthesis section is then concentrated gradually—the unconverted reactants being recovered in one or more recovery sections—and is solidified in follow-up finishing (e.g., prilling, granulating, . . . ) sections.

In one known configuration, the reactants, which are recirculated to the synthesis section, are recovered in a quantity or number of sections, and more specifically in a high-pressure, medium-pressure, and low-pressure section.

A urea production plant normally produces gas streams containing unconverted reactants, including non-reacted ammonia, and so produces vent gases containing ammonia.

More specifically, the medium-pressure section vents continuous gas streams containing small amounts of ammonia and hydrogen, as well as methane and inerts (mainly nitrogen). Depending on the process used in the urea production plant, these gas streams may also contain oxygen.

The gas streams are normally mixed to conform with safety regulations, and more specifically to remain outside explosion limits.

The ammonia in the gas streams produced in the urea plant, particularly the medium-pressure section, must therefore be removed before releasing the gas streams into the atmosphere.

One fairly commonly used system for preventing ammonia emission into the atmosphere employs a torch, into which the gases (ammonia, methane, oxygen, hydrogen and inerts) from the medium-pressure section (or urea plant in general) are fed continuously. The gases are fed to the end of the torch, where a gas- (e.g., methane-) fuelled flame burns the ammonia in uncontrolled manner.

PCT Patent Application No. WO2012134288 describes a system based on the use of an incinerator, where a gas stream, rich in ammonia and hydrogen and coming from a urea production process not requiring passivating oxygen, is burned, producing a small amount of NOx; and the ammonia content is further removed, if necessary, using selective catalytic reduction (SCR) or selective non-catalytic reduction (SNCR) processes.

Known systems have various drawbacks, and in particular:

the formation of large amounts of nitric oxide (NOx), in the case of uncontrolled ammonia combustion, with the risk of emitting NOx into the atmosphere;

relatively high cost, due to the continuous fuel (e.g., methane) supply necessary to keep the torch alight, and to the SCR catalyst for removing the nitric oxides produced;

the relative complexity of the process as a whole, operating with no passivating oxygen and with the need for an incinerator.

SUMMARY

The present disclosure relates to a method and system configured to remove ammonia from a continuous vent gas stream of a urea plant (i.e., urea production plant).

More specifically, the disclosure relates to a method and system configured to remove small amounts of ammonia from a continuous vent gas stream of a medium-pressure section of a urea plant.

It is an advantage of the present disclosure to provide a method and system configured to remove ammonia from a continuous vent gas stream of a urea plant, in particular of a medium-pressure section of a urea plant, and which provide for reducing, and in certain embodiments eliminating, ammonia emissions from a urea production plant relatively cheaply and relatively easily.

In certain embodiments, the present disclosure therefore relates to a method of removing ammonia from a continuous vent gas stream of a urea plant including removing ammonia from the continuous vent gas stream of the urea plant utilizing a controlled-combustion process in which ammonia is oxidized. The continuous vent gas stream of the urea plant including passivating oxygen used in the urea plant, wherein the passivating oxygen exploited to remove the ammonia from the continuous vent gas stream of the urea plant. The controlled-combustion process of this embodiment includes at least a first combustion performed: (i) in the presence of an understoichiometric amount of oxygen acting as the sole comburent, and (ii) in a hydrogen-containing reducing atmosphere which favors oxidation of ammonia to nitrogen to reduce the formation of nitric oxides.

The disclosure is particularly advantageous for removing ammonia from oxygen-containing continuous vent gas streams from the urea production plant, as in the case of urea production processes employing passivating oxygen (i.e., processes in which oxygen is added to the synthesis reactor supply to passivate metal (typically, stainless steel) surfaces).

It should be appreciated that mainly due to the intermediate formation of ammonium carbamate, the carbon dioxide-ammonia reaction produces highly corrosive conditions capable of even corroding stainless steel normally used in these applications. Adding small amounts of oxygen provides for passivating and so preventing corrosion of the stainless steel surfaces.

Examples of urea production plants employing oxygen can be found in PCT Patent Application No. WO2010/006757 and PCT Patent Application No. WO2008/141832.

In processes of this type, the vent gas streams for treatment (which are normally pre-mixed to remain below explosion limits) therefore substantially contain: ammonia, hydrogen, methane, inerts (mainly nitrogen), and even a significant percentage of oxygen (though still below explosion limits).

The vent gas stream from a urea plant (in particular, the medium-pressure section) typically has the following composition (percentages in volume, 1200 Nm3/h at 50° C., 0.1 MPa(g)):

NH3 1.3%
H2 12.0%
N2 59.7%
O2 14.8%
Ar 1.8%
CH4 10.4%.

In accordance with certain embodiments of the disclosure, the passivating oxygen already present in the urea plant is exploited to remove ammonia. In other words, in accordance with the disclosure, ammonia is eliminated from the continuous vent gas streams from the urea production plant using a controlled-combustion process performed in at least a first lean, (i.e., oxygen-poor) combustion step, in which an understoichiometric (i.e., less than stoichiometric) amount of the oxygen in the gas stream containing ammonia for removal is used as the sole comburent (combustion supporter), and in the presence of hydrogen (i.e., in a reducing atmosphere). The hydrogen (acting as fuel) that is also already present in the gas stream to treat, serves to eliminate the few nitric oxides (NOx) that may be formed.

In certain embodiments, ammonia is advantageously removed in at least two combustion stages (though not necessarily) performed in one combustion environment.

The combustion reaction is therefore performed in controlled manner in two steps or stages:

a first oxygen-poor (lean) combustion step performed in the presence of an understoichiometric (i.e., less than stoichiometric) amount of oxygen and in a hydrogen-containing reducing atmosphere (reducing atmosphere of hydrogen); at this first step, an understoichiometric amount of the oxygen in the gas stream for treatment is used as the sole comburent (combustion supporter); and the hydrogen (acting as fuel) that is also already present in the gas stream for treatment, serves to eliminate the few nitric oxides (NOx) that may be formed; and a second step performed in the presence of a stoichiometric or even greater amount of oxygen, to burn all the remaining gases (in particular, methane and hydrogen); this second step is performed with the addition of secondary air or oxygen to complete combustion of the unburned gases (mainly hydrogen and methane) in the gases from the first step.

Combustion in accordance with certain embodiments of the disclosure is defined as controlled, in that dividing combustion into steps as described above controls the formation and elimination of nitric oxides (NOx), using understoichiometric combustion and the presence of hydrogen respectively, and so reduces nitric oxide emission into the atmosphere.

The reactions occurring during the combustion process are as follows:

$$4NH_3 + 3O_2 \rightarrow 2N_2 + 6H_2O \text{ (favored)} \quad (1)$$

$$2NH_3 + 2O_2 \rightarrow N_2O + 3H_2O \text{ (unfavored)} \quad (2)$$

$$4NH_3 + 5O_2 \rightarrow 4NO + 6H_2O \text{ (unfavored)} \quad (3)$$

$$2NO + O_2 \rightarrow 2NO_2 \text{ (unfavored)} \quad (4)$$

$$NO + H_2 \rightarrow N_2 + H_2O \text{ (favored)} \quad (5)$$

$$2NO_2 + 2H_2 \rightarrow N_2 + 2H_2O \text{ (favored)} \quad (6)$$

Controlled combustion in accordance with the disclosure does not actually need two combustion chambers. The two steps may be performed in one combustion environment, or in separate combustion chambers.

The disclosure may be implemented in various ways. For example:

(A) catalytic controlled combustion in two sections, with understoichiometric oxygen in the first section, and stoichiometric or overstoichiometric oxygen in the second section;

(B) non-catalytic controlled combustion in a burner, in two sections, with understoichiometric oxygen and possibly steam injection in the first section, and stoichiometric or overstoichiometric oxygen in the second section; and (C) understoichiometric oxygen catalytic controlled combustion in one section.

More specifically, in a first embodiment (A), the two combustion steps are performed using respective catalytic oxidations with no flame, and using appropriate respective catalysts. To initiate the catalytic reactions, only a small amount of heat, supplied for example by a heating resistor (with no flame needed), is required at the start of the process (to reach a predetermined activation temperature of about 150° C.). During steady, normal operation, on the other hand, no further heat or additional fuel is needed (as stated, the fuel needed is already present in the gas stream for treatment); and secondary air is only supplied at the second step, to sustain the reaction of the second catalyst.

The first step employs one or more catalysts that promote understoichiometric catalytic oxidation of ammonia in a reducing atmosphere, and favored reaction (1) above over the others, particularly those forming nitric oxides, at temperatures ranging roughly between 150° C. and 400° C.

Examples of specific ammonia oxidation catalysts are those in the 'ammonia SCO' (ammonia Selective Catalytic Oxidation) class used for selective ammonia catalytic oxidation, and which are usable in this case, seeing as the continuous gas streams treated already contain the oxygen needed to burn the ammonia, and catalytic reactions (5) and (6) above are strongly favored by the hydrogen already present in the gas streams, and which reduces the formation of nitric oxides (NOx) and eliminates the few formed.

Once the ammonia is removed, methane and hydrogen can be removed with a second catalytic oxidation. Because ammonia has been eliminated by the previous ammonia and hydrogen catalytic oxidation reactions, nitric oxide formation in the second oxidation is limited. Catalytic methane combustion acts at a temperature of roughly 500° C. to 600-700° C. (the heat needed to initiate catalytic methane combustion is generated by the previous oxidation reaction and by catalytic oxidation of hydrogen).

Before the gases, cleansed of ammonia, methane and hydrogen, are released into the atmosphere, part of the heat produced in the two catalytic beds may be recovered to produce steam or to preheat air for supply to the finishing unit (e.g., granulating or prilling unit, where the urea produced is formed into granules or prills) of the urea production plant.

A second embodiment (B) employs a premixed burner for controlled combustion in two steps or stages:

a first step or stage, in which lean combustion is performed in the presence of oxygen and hydrogen already present in the gas stream for treatment; and a second step or stage, in which secondary air is injected.

Lean combustion favors reaction (1) and impedes reactions (2) and (3) above (i.e., favors oxidation of ammonia to nitrogen, and impedes and strongly reduces the formation of nitric oxides).

Ammonia is oxidized at the first step, which employs the oxygen already present in the continuous gas streams from the urea production plant, thus enabling lean combustion (i.e., in the presence of understoichiometric oxygen, unlike the conventional torch system, in which combustion is performed in an excess of oxygen).

At the first stage, it is mainly the presence of hydrogen which favors the destruction-elimination of any nitric oxides formed, thus favoring reactions (5) and (6) above.

Understoichiometric combustion enables a reduction in flame temperature with respect to overstoichiometric combustion (as in a torch), thus further reducing the formation of NOx.

To further reduce the formation of nitric oxides, steam may be injected at the first oxidation step. Injecting steam further reduces the flame temperature, to impede the formation of nitric oxides.

Methane and hydrogen combustion is completed at the second stage, in which secondary air or oxygen is supplied.

Part of the combustion-generated heat may be recovered in a boiler configured to produce steam. Once the heat is recovered, the clean gases may be released into the atmosphere.

As opposed to recovering heat in a boiler, all the heat generated in the premixed burner by combustion-oxidation may be recovered to heat the atomizing air for the granulating unit, or the fluidizing air for use in the urea plant prilling unit fluid beds (normally at a temperature of about 135° C.), thus reducing cost by eliminating the need for a special steam air preheater.

In a third embodiment (C), particularly suitable for 'revamping' existing plants equipped with torches, the vent gas stream for treatment, as opposed to being fed to the torch, is diverted to an integrated unit comprising a heat exchanger (e.g., plate type exchanger), and a catalytic cartridge containing the first-step (e.g., 'ammonia SCO') catalyst. As stated, the catalyst provides for eliminating solely ammonia by understoichiometric combustion in a reducing atmosphere, and impeding the formation of nitric oxides. This embodiment does not include secondary-air supply and, therefore, the second combustion-oxidation step, in that the oxygen contained in the continuous gas streams from the urea plant is sufficient to completely oxidize the ammonia at the first (and only) step. This solution is relatively extremely cheap and relatively compact, not least of all by requiring no additional secondary combustion air lines and equipment (e.g., boilers and fans), and is therefore particularly suitable for 'revamping' existing plants, in which the existing torch is replaced with a new integrated unit.

Additional features and advantages are described in, and will be apparent from the following Detailed Description and the figures.

BRIEF DESCRIPTION OF THE DRAWINGS

A number of non-limiting embodiments of the present disclosure will be described by way of example with reference to the attached drawings, in which.

DETAILED DESCRIPTION

Referring now to the example embodiments of the present disclosure illustrated in FIGS. 1 to 6, FIG. 1 shows a highly schematic, simplified block diagram of a urea plant 1 (i.e., urea production plant).

Figure 1:
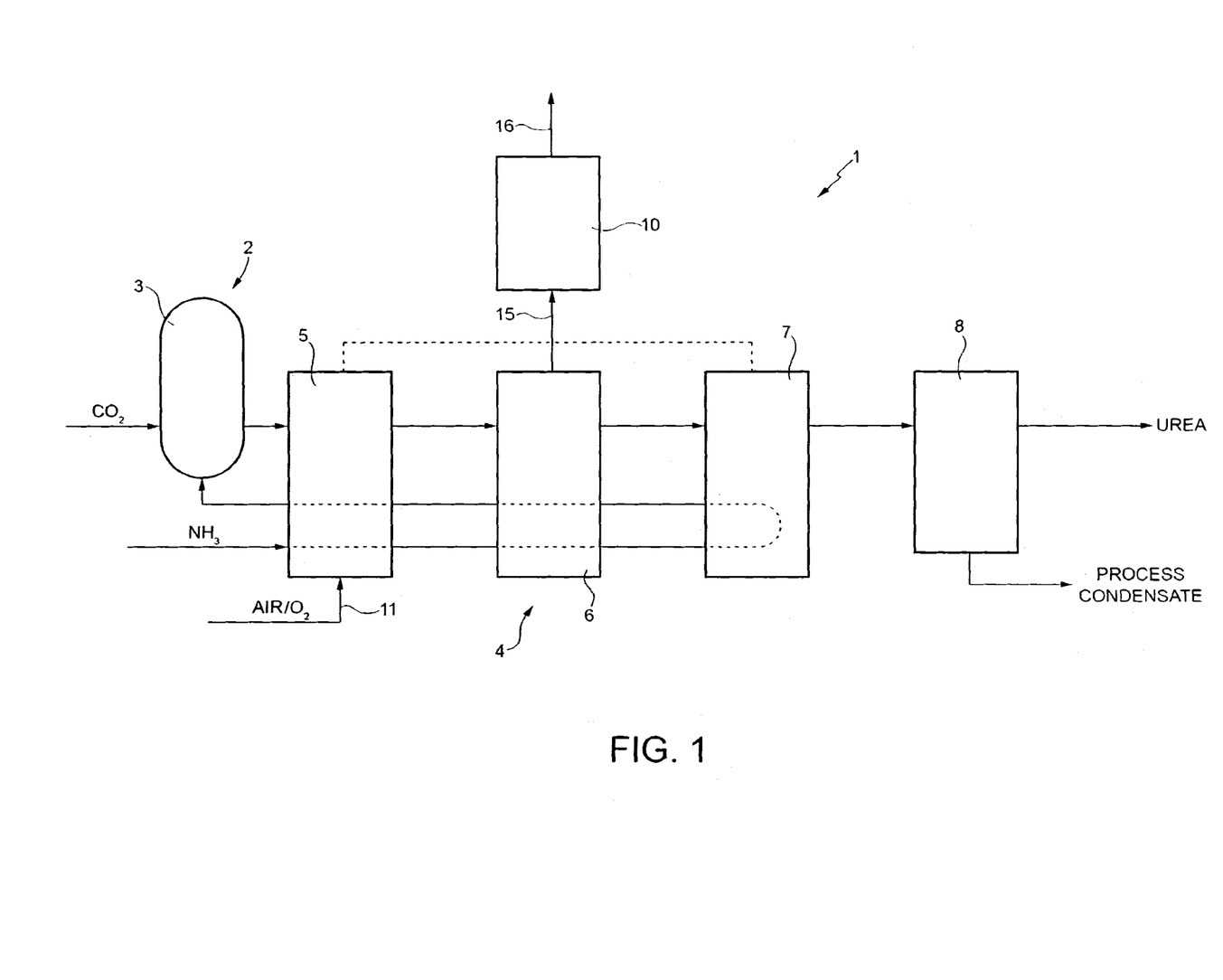
FIG. 1 shows a highly schematic, simplified block diagram of a urea production plant equipped with an ammonia removal system in accordance with the disclosure.

Urea plant 1 is, for example, of the type described in PCT Patent Application No. WO2010/006757 and PCT Patent Application No. WO2008/141832, the content of which are each included herein by way of reference.

In certain embodiments, urea plant 1 substantially comprises: a synthesis section 2 with a urea synthesis reactor 3 where the urea synthesis reaction from ammonia and carbon dioxide takes place; recovery sections 4—more specifically, a high-pressure section 5, medium-pressure section 6, and low-pressure section 7—where the urea solution from synthesis section 2 is gradually concentrated, non-reacted ammonia and carbon dioxide are removed, and the recovered components are recirculated; and finishing sections 8 including at least one finishing unit (e.g., a granulating or prilling unit where the urea produced is formed into granules or prills).

For the sake of simplicity, the component parts of each section and the lines supplying and recirculating the various gas streams from one section to another are not shown in detail in FIG. 1, which simply shows schematically the reactant feed lines to urea plant 1, and the operating connections between the sections.

Urea plant 1 is equipped with an ammonia removal system 10 configured to process ammonia-containing vent gas steams produced in urea plant 1.

System 10 is connected to urea plant 1 (e.g., to medium-pressure section 6 (or optionally to other sections)) to tap a continuous vent gas stream.

A typical continuous vent gas stream from medium-pressure section 6 of urea plant 1 contains ammonia, hydrogen, methane and inerts (mainly nitrogen).

If, advantageously for the present disclosure, urea plant 1 implements a process employing passivating oxygen supplied to urea plant 1 by an air or oxygen feed line 11, the vent gas streams also contain oxygen.

The vent gas stream fed to system 10 is of such a composition—possibly adjusted by mixing the various component streams—as to be outside explosion limits.

Figure 2:
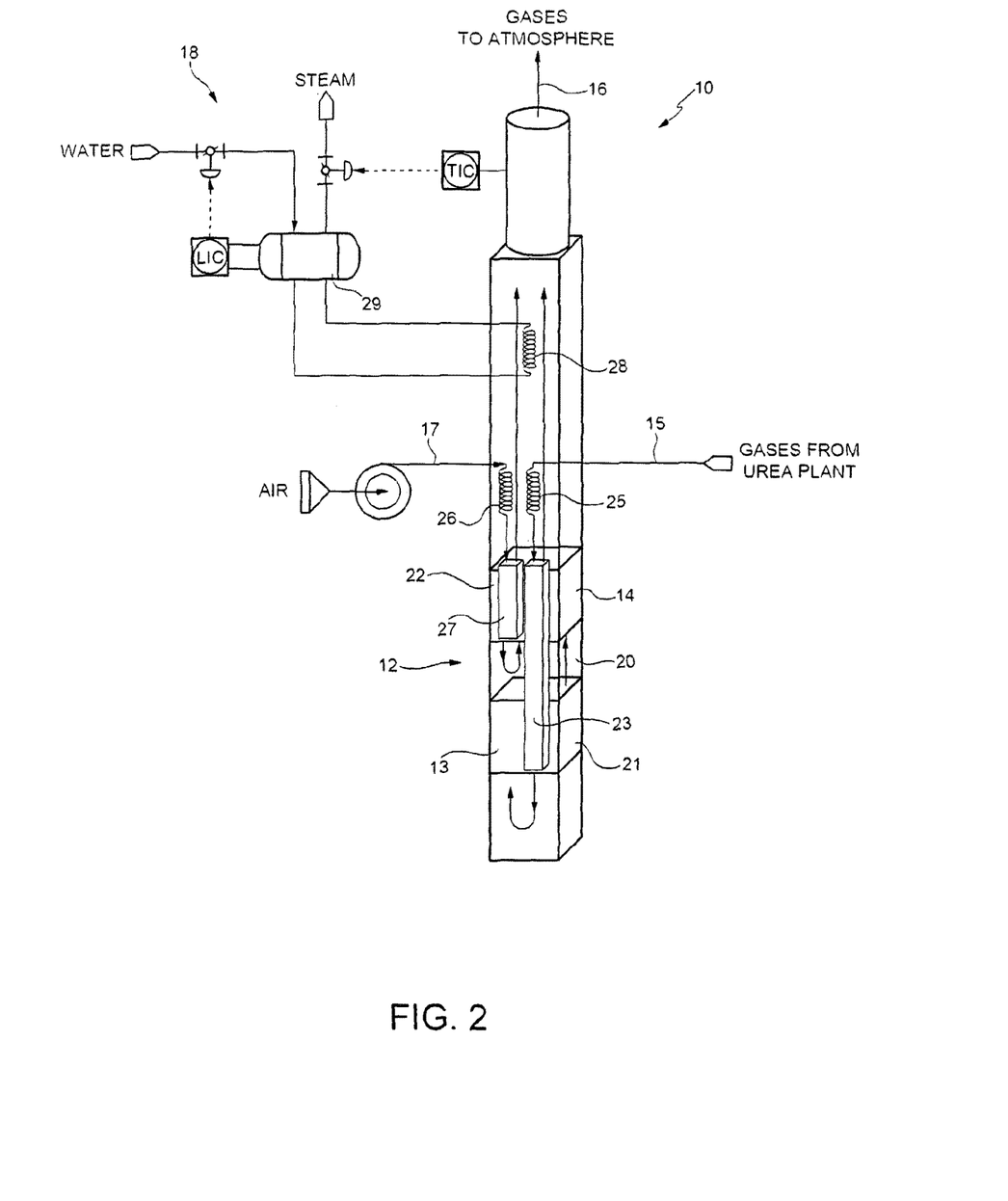
FIG. 2 shows a schematic of a first embodiment of the ammonia removal system according to the disclosure.

In the FIG. 2 embodiment (A), system 10 comprises: a treating unit 12 having a first and second oxidation section 13, 14; an inlet line 15 connecting treating unit 12 to urea plant 1 (more specifically, to medium-pressure section 6) and supplying treating unit 12 with the gas stream for treatment; an outlet line 16 configured to vent (e.g., into the atmosphere), the gas treated by treating unit 12; a secondary-air circuit 17 configured to feed air to treating unit 12; and a heat recovery circuit 18 configured to recover heat from treating unit 12.

Treating unit 12 comprises a reaction chamber 20 (defined by one or by two connected chambers) where controlled combustion of the gas stream for treatment is performed. Treating unit 12 is configured to perform a catalytic controlled combustion of the ammonia contained in the gas stream for treatment. Controlled combustion is performed in two steps, in oxidation sections 13 and 14 respectively, with understoichiometric oxygen in the first section 13, and stoichiometric or overstoichiometric oxygen in the second section 14.

More specifically, sections 13, 14 have respective catalytic beds 21, 22 arranged in series with respect to the gas stream circulating in reaction chamber 20.

Generally, the gas stream flows into reaction chamber 20 from a central inlet, is fed by a feed pipe 23 to one end of reaction chamber 20, past first oxidation section 13 and its catalytic bed 21, and then flows successively through first oxidation section 13 and second oxidation section 14 (and respective catalytic beds 21, 22).

As shown by way of example in FIG. 2, oxidation sections 13, 14 and respective catalytic beds 21, 22 are arranged one over the other inside a substantially vertical reaction chamber 20. It is understood, however, that sections 13, 14 and respective catalytic beds 21, 22 may be arranged differently (e.g., side by side horizontally in a substantially horizontal reaction chamber 20). The gas stream for treatment is fed by feed pipe 23 to the bottom (or at any rate to one end) of reaction chamber 20, and then flows first through first oxidation section 13, and then through second oxidation section 14 (and respective catalytic beds 21, 22).

The gas stream for treatment is preheated by the gases from second oxidation section 14 in a heat exchanger 25 located past second oxidation section 14 (above second oxidation section 14 in the FIG. 2 example with a vertical reaction chamber 20).

Catalytic beds 21, 22 comprise appropriate respective catalysts configured to activate the two combustion steps (i.e., respective flameless catalytic oxidations). To reach the activating temperature of around 150° C. and initiate the catalytic reactions, heat is only supplied at the start, utilizing an initiating or preheating device (with no flame needed) such as an electric resistor (not shown in the drawings). Once initiated, the reactions are self-sustaining, by recovering heat from the burnt gases.

No external fuel need be added, since the fuel used is present in the gas stream for treatment.

In the first oxidation section 13 there are catalysts (one or more) that promote understoichiometric catalytic oxidation of ammonia in a reducing atmosphere, and possibly also oxidation of part of the hydrogen.

Secondary air is fed into second section 14 by secondary-air circuit 17. The secondary air is preheated by the gases from second oxidation section 14 in a heat exchanger 26 at the outlet of second oxidation section 14, and is fed past (below, in the case of a vertical reaction chamber 20) catalytic bed 22 of second oxidation section 14 by an air pipe 27 through catalytic bed 22.

Catalytic oxidation to remove methane and hydrogen takes place in second oxidation section 14.

Heat recovery circuit 18 serves to recover heat from the ammonia-, methane- and hydrogen-free gases produced by catalytic beds 21, 22, before the gases are released into the atmosphere by outlet line 16. Heat recovery circuit 18 comprises, for example, a heat exchanger 28 in series with catalytic beds 21, 22, to draw heat from the gases from the beds, and produce steam in a boiler 29.

Heat from the gases from oxidation sections 13, 14 may also be used to preheat air for finishing sections 8, and in particular for the granulating or prilling unit of urea plant 1.

For example, the gases from oxidation sections 13, 14, and more specifically from second oxidation section 14 (the ammonia-, methane- and hydrogen-free gases from catalytic beds 21, 22), may be diluted (i.e., mixed directly, without passing through a heat exchanger) with air for use as atomizing air in the granulating unit, or as fluidizing air in the prilling unit of urea plant 1, for the purpose of raising the air temperature.

Figure 3:
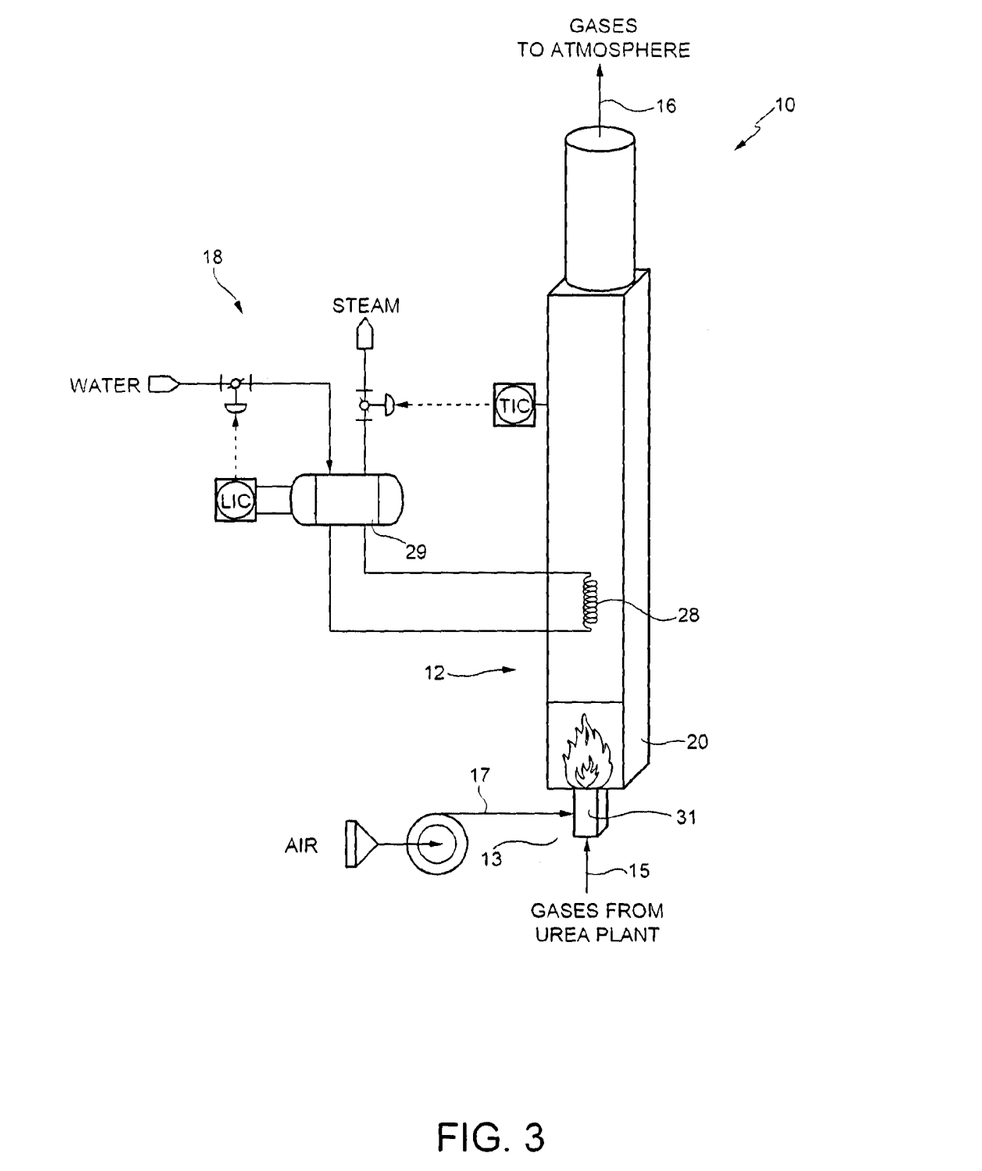
FIG. 3 shows a schematic of a second embodiment of the ammonia removal system according to the disclosure.

In the FIG. 3 embodiment (B), in which details similar or identical to those already described are indicated using the same reference numbers, removal system 10 comprises: a treating unit 12 with a reaction chamber 20; an inlet line 15 connecting treating unit 12 to urea plant 1 (more specifically, to medium-pressure section 6) and supplying treating unit 12 with the gas stream for treatment; an outlet line 16 configured to vent (e.g., into the atmosphere) the gas treated by treating unit 12; a secondary-air circuit 17 configured to feed air to treating unit 12; and a heat recovery circuit 18 configured to recover heat from treating unit 12. In this embodiment, treating unit 12 comprises a reaction chamber 20 where controlled combustion of the gas stream for treatment is performed, but, in this case, treating unit 12 is configured for non-catalytic combustion.

Figure 4:
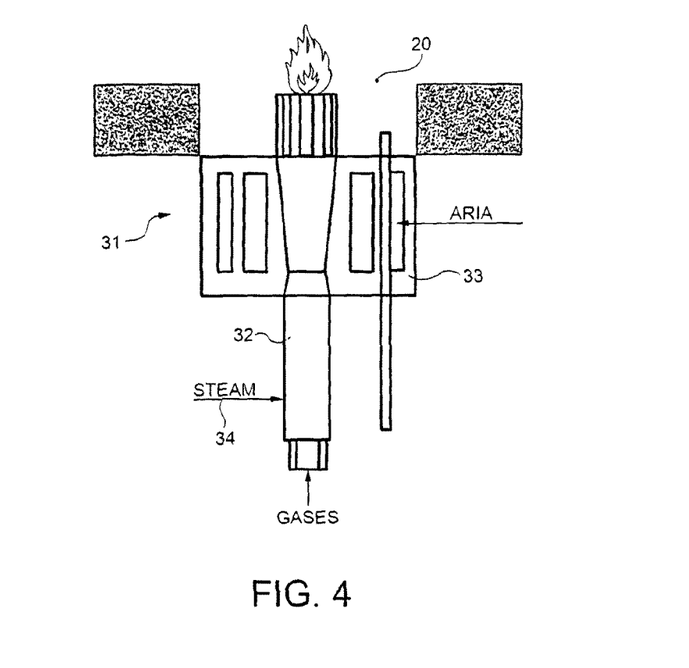
FIG. 4 shows a larger-scale schematic of a detail of the FIG. 3 ammonia removal system.

More specifically, and with reference also to FIG. 4, treating unit 12 comprises a premixed burner 31 located, for example, at one end (e.g., the bottom end) of reaction chamber 20, and configured to perform controlled combustion in two steps in respective stages 32, 33 of burner 31:

a first lean combustion step (first stage 32) in the presence of hydrogen and understoichiometric oxygen already present in the gas stream for treatment;

a second step (second stage 33) in which secondary air is injected by secondary-air circuit 17, so combustion takes place in the presence of a stoichiometric or overstoichiometric amount of oxygen.

Inlet line 15 feeds the vent gas stream for treatment to first stage 32 of burner 31; and secondary-air circuit 17 feeds secondary air to second stage 33 of burner 31, where methane and hydrogen combustion is completed.

Steam may also be injected optionally into first stage 32 by a steam line 34. In this embodiment, heat recovery circuit 18 recovers heat from the gases burnt in reaction chamber 20, before they are released into the atmosphere by outlet line 16. Heat recovery circuit 18 comprises, for example, a heat exchanger 28 housed inside reaction chamber 20 to draw heat from the gases burnt by burner 31, and produce steam in a boiler 29 and/or preheat air for finishing sections 8, and in particular for the granulating or prilling unit of urea plant 1.

Alternatively, heat from the gases burnt in reaction chamber 20 may be recovered directly, without going through a heat exchanger, to preheat air for finishing sections 8, and in particular for the granulating or prilling unit of urea plant 1.

Figure 5:
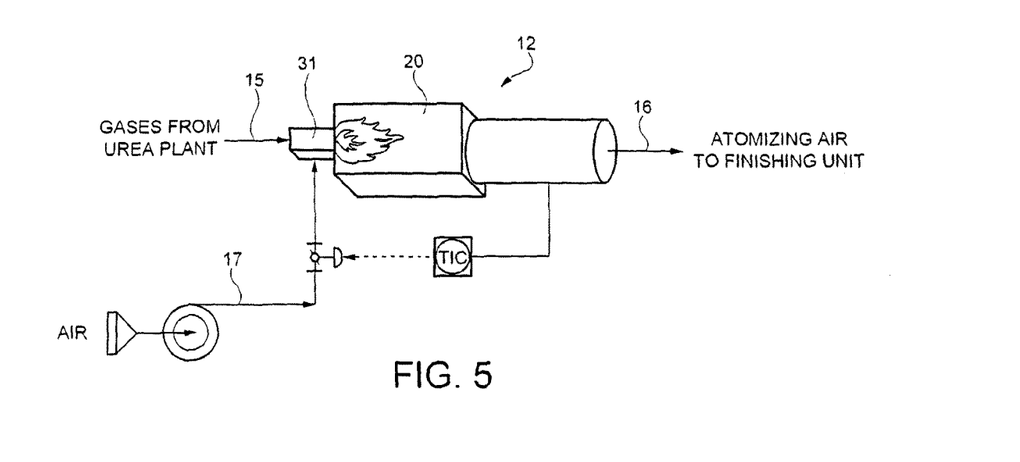
FIG. 5 shows a schematic of a variation of the FIG. 3 embodiment.

For example, as shown in FIG. 5, the burnt gases from burner 31 are diluted (i.e., mixed directly, without passing through a heat exchanger) with air for use as atomizing air in the granulating unit, or as fluidizing air in the prilling unit of urea plant 1, for the purpose of raising the air temperature. Outlet line 16 therefore connects to an air feed line of the granulating or prilling unit.

Figure 6:
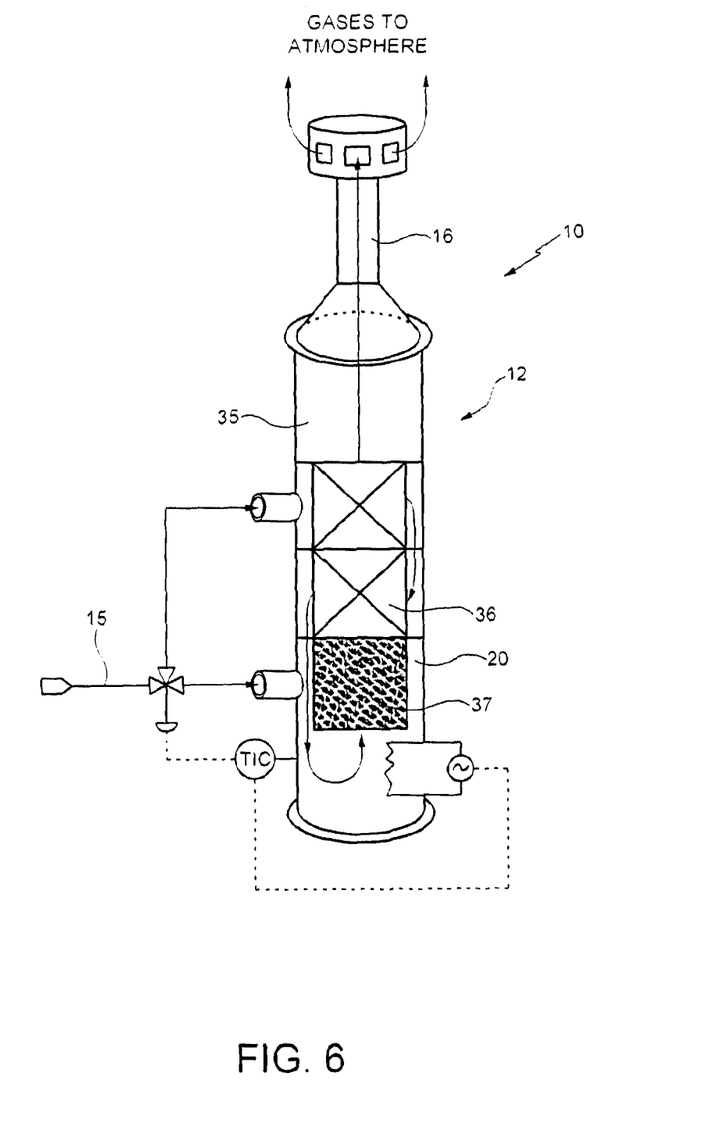
FIG. 6 shows a schematic of a third embodiment of the ammonia removal system according to the disclosure.

In the FIG. 6 embodiment (C), in which details similar or identical to those already described are indicated using the same reference numbers, removal system 10 comprises: a treating unit 12 with a reaction chamber 20; an inlet line 15 connecting treating unit 12 to urea plant 1 (more specifically, to medium-pressure section 6) and supplying treating unit 12 with the gas stream for treatment; and an outlet line 16 configured to vent (e.g., into the atmosphere) the gas treated by treating unit 12.

Treating unit 12 comprises a reaction chamber 20 where controlled combustion of the gas stream for treatment is performed. Treating unit 12 is configured to perform catalytic combustion of ammonia in the gas stream for treatment, with an understoichiometric amount of oxygen. In other words, this embodiment only performs the first step in the process described with reference to the first embodiment in FIG. 2.

System 10 comprises an integrated unit 35 comprising a heat exchanger 36 (e.g., a plate exchanger) and a catalytic cartridge 37 containing the catalyst (e.g., 'ammonia SCO' catalyst) for the first step described above. The catalyst eliminates ammonia and possibly also part of the hydrogen (to promote reactions (1), (5) and (6) indicated above, and impede the others) by understoichiometric combustion in a reducing atmosphere, and impedes the formation of nitric oxides.

The gas stream for treatment flows along inlet line 15 into unit 35, and through heat exchanger 36 to catalytic cartridge 37 in reaction chamber 20, where controlled combustion as described above takes place. The hot reacted gas from catalytic cartridge 37 flow through heat exchanger 36 to preheat the gas stream for treatment.

This embodiment does not include secondary-air supply and, therefore, the second combustion-oxidation step described above. The oxygen in the treated gas stream is sufficient to completely oxidize the ammonia.

Clearly, further changes may be made to the method and system as described herein without, however, departing from the scope of the accompanying Claims. That is, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of removing ammonia from a continuous vent gas stream of a urea plant, said method comprising:
removing ammonia from the continuous vent gas stream of the urea plant utilizing a controlled-combustion process in which ammonia is oxidized, wherein:
(a) said continuous vent gas stream of the urea plant includes:
(i) passivating oxygen used in the urea plant, wherein said passivating oxygen is already present in the continuous vent gas stream prior to being exploited to remove said ammonia from the continuous vent gas stream of the urea plant, and no additional passivating oxygen is added to the continuous vent gas stream prior to the already present passivating oxygen being exploited to remove said ammonia from the continuous vent gas stream of the urea plant, and
(ii) hydrogen already present in the continuous vent gas stream prior to being exploited to reduce a formation of nitric oxides, wherein the hydrogen acts as a fuel of a first combustion with no additional fuel being added to the continuous vent gas stream for the first combustion, and
(b) said controlled-combustion process includes at least the first combustion performed:
(i) in the presence of an understoichiometric amount of oxygen needed in the first combustion to oxidize ammonia and acting as the sole comburent, and
(ii) in a hydrogen-containing reducing atmosphere which favors oxidation of ammonia to nitrogen to reduce the formation of nitric oxides.

2. The method of claim 1, wherein the hydrogen-containing reducing atmosphere impedes the formation of nitric oxides.

3. The method of claim 1, wherein at least part of the continuous vent gas stream of the urea plant includes a continuous vent gas stream of a medium-pressure section of the urea plant.

4. The method of claim 1, wherein the controlled-combustion process includes a second combustion performed in the presence of a stoichiometric amount of oxygen to burn gases remaining from the first combustion.

5. The method of claim 1, wherein the controlled-combustion process includes a second combustion performed in the presence of an overstoichiometric amount of oxygen.

6. The method of claim 4, wherein the second combustion is performed to burn methane and hydrogen remaining from the first combustion.

7. The method of claim 4, wherein said second combustion is performed with the addition of one of secondary air and oxygen to complete combustion of unburned gases from the first combustion.

8. The method of claim 1, wherein said first combustion includes understoichiometric oxygen catalytic oxidation.

9. The method of claim 1, wherein the controlled-combustion process includes two catalytic oxidation steps performed in respective oxidation sections with an understoichiometric amount of oxygen in the first oxidation section, and one of a stoichiometric amount of oxygen and an over-stoichiometric amount of oxygen in the second oxidation section.

10. The method of claim 1, wherein the controlled-combustion process includes a non-catalytic combustion in a burner, said non-catalytic combustion performed in a first stage with an understoichiometric amount of oxygen, and in a second stage with one of: a stoichiometric amount of oxygen and an overstoichiometric amount of oxygen.

11. The method of claim 10, wherein the controlled-combustion process is performed utilizing a two-stage pre-mixed burner.

12. The method of claim 10, wherein the first combustion is performed in the first stage in the presence of hydrogen, and the understoichiometric amount of oxygen is from said continuous vent gas stream of the urea plant, and which includes injecting one of secondary air and oxygen to complete combustion of methane and hydrogen.

13. The method of claim 10, which includes injecting steam in the first stage.

14. The method of claim 1, which includes recovering heat from any gases cleansed of ammonia, methane and hydrogen to produce at least one of steam and pre-heat air to supply to a finishing unit, wherein said heat is recovered before said cleansed gases are released into the atmosphere.

15. The method of claim 14, wherein the finishing unit includes one of a granulating unit of the urea plant and a prilling unit of the urea plant.

16. The method of claim 1, wherein the first combustion includes a lean, oxygen-poor combustion.

17. A method of removing ammonia from a continuous vent gas stream of a urea plant, said method comprising:
removing ammonia from the continuous vent gas stream of a medium-pressure section of the urea plant utilizing a controlled-combustion process in which ammonia is oxidized, said continuous vent gas stream of the urea plant including:
passivating oxygen used in the urea plant, wherein said passivating oxygen is already present in the continuous vent gas stream prior to being exploited to remove said ammonia from the continuous vent gas stream of the urea plant, and no additional passivating oxygen is added to the continuous vent gas stream prior to the already present passivating oxygen being exploited to remove said ammonia from the continuous vent gas stream of the urea plant, and hydrogen already present in the continuous vent gas stream prior to being exploited to reduce a formation of nitric oxides, wherein the hydrogen acts as a fuel of a first lean, oxygen-poor combustion with no additional fuel being added to the continuous vent gas stream for the first combustion, said controlled-combustion process including:

at least the first lean, oxygen-poor combustion performed:
  (i) in the presence of an understoichiometric amount of oxygen acting as the sole comburent, and
  (ii) in a hydrogen-containing reducing atmosphere which favors oxidation of ammonia to nitrogen to reduce the formation of nitric oxides and impedes the formation of nitric oxides, and   a second combustion performed in the presence of a stoichiometric amount of oxygen and with the addition of one of secondary air and oxygen to complete combustion of unburned methane and hydrogen remaining from the first combustion.

18. The method of claim 17, wherein said first combustion includes understoichiometric oxygen catalytic oxidation.

19. The method of claim 17, wherein the controlled-combustion process includes two catalytic oxidation steps performed in respective oxidation sections with an understoichiometric amount of oxygen in the first oxidation section, and one of a stoichiometric amount of oxygen and an over-stoichiometric amount of oxygen in the second oxidation section.

20. The method of claim 17, wherein the controlled-combustion process includes a non-catalytic combustion in a burner, said non-catalytic combustion performed in a first stage with an understoichiometric amount of oxygen, and in a second stage with one of: a stoichiometric amount of oxygen and an overstoichiometric amount of oxygen.

* * * * *